United States Patent [19]

Decorzant et al.

[11] Patent Number: 5,268,356
[45] Date of Patent: Dec. 7, 1993

[54] CYCLIC TERTIARY ALCOHOLS AND THEIR USE AS PERFUMING INGREDIENTS

[75] Inventors: René Decorzant, Onex; Ferdinand Naef, Carouge, both of Switzerland

[73] Assignee: Firmenich SA, Geneva, Switzerland

[21] Appl. No.: 969,909

[22] Filed: Nov. 2, 1992

[30] Foreign Application Priority Data

Nov. 25, 1991 [CH] Switzerland ............ 3444/91

[51] Int. Cl.$^5$ ................................ A61K 7/46
[52] U.S. Cl. ............................ 512/23; 568/825; 568/834
[58] Field of Search ............ 512/23; 568/825, 834

[56] References Cited

U.S. PATENT DOCUMENTS

| | | | |
|---|---|---|---|
| 3,852,219 | 12/1974 | Nikawitz et al. | 512/23 |
| 4,072,723 | 2/1978 | Wehrli . | |
| 4,261,867 | 4/1981 | Frankhauser et al. | 512/23 |
| 4,719,041 | 1/1988 | Schaper et al. | 512/23 |

FOREIGN PATENT DOCUMENTS

| | | | |
|---|---|---|---|
| 2444585 | 4/1976 | Fed. Rep. of Germany | 568/825 |
| 2547223 | 5/1977 | Fed. Rep. of Germany | 568/825 |

OTHER PUBLICATIONS

Braish et al, Chem. Abst., vol. 18,666p (1987).
Lomas et al, J. Org. Chem., vol. 44, pp. 1647-1654 (1979).
Mitchell et al, Tet Letters, vol. 25, pp. 907-910 (1984).
Chemical Abstracts Registry Service No. 105875-60-3 (1986).
March, J., "Advanced Organic Chemistry", 3rd ed., p. 817, Wiley Interscience, N.J. (1985).
Kopf, H. et al., *Liebigs Ann. Chem.*, 943, 1987.

*Primary Examiner*—James H. Reamer
*Attorney, Agent, or Firm*—Pennie & Edmonds

[57] ABSTRACT

The cyclic tertiary alcohols of formula

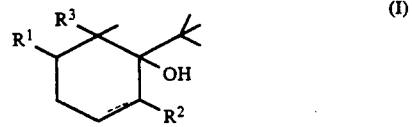

(I)

wherein the dotted line indicates the location of a single or double bond, symbols $R^1$ and $R^3$ represent each a hydrogen atom or a methyl radical and symbol $R^2$ stands for a lower alkyl radical, are useful perfuming ingredients for the preparation of perfuming compositions and perfumed articles, to which they impart odor notes of the patchouli type.

8 Claims, No Drawings

CYCLIC TERTIARY ALCOHOLS AND THEIR USE AS PERFUMING INGREDIENTS

BRIEF DESCRIPTION OF THE INVENTION

The present invention relates to the field of perfumery. It concerns, more particularly, novel compounds of formula

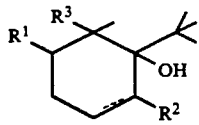

wherein the dotted line indicates the location of a single or double bond, symbols $R^1$ and $R^3$ represent each a hydrogen atom or a methyl radical and symbol $R^2$ represents a lower alkyl radical. The latter is here defined as an alkyl radical which has 1 to 6, preferably 1 to 3, carbon atoms.

The invention also provides a method to confer, improve, enhance or modify the odor properties of a perfuming composition or a perfumed article, which method comprises adding to said composition or article a fragrance effective amount of a compound of formula (I) as defined above.

A further object of the invention is a perfuming composition or a perfumed article containing as a perfuming ingredient a compound of formula (I) as defined above.

THE INVENTION

It has now been discovered that compounds (I) cited above possess very useful odor properties and that, as a result, they can be used for the preparation of perfuming compositions and perfumed articles, to which they impart odor notes reminiscent of the odor of patchouli essential oil.

Amongst the compounds of formula (I), one can cite, as a preferred compound, 1-tert-butyl-2,6,6-trimethyl-2-cyclohexen-1-ol. This compound possesses a very useful patchouli-type odor note, together with a camphor, woody-powdery and damascone-like fragrance character. It is, in fact, an odor note which recalls the underwood and resinous parts of patchouli, while having a less earthy character.

It is known that this type of odor note is, in fact, extremely rare amongst the compounds of synthetic origin, which renders the odor of 1-tert-butyl-2,6,6-trimethyl-2-cyclohexen-1-ol all the more useful. In addition, although the patchouli-type odor note is one of the most important in perfumery, the synthetic components of patchouli oil, such as patchoulol or patchoulenol, are so difficult to prepare that they turn out to be non competitive from a price point of view. If one further considers the problems related to the fluctuations inherent to the production of the natural origin essential oil, one becomes even more aware of the importance that may assume the discovery of a synthetic origin compound which possesses odor properties capable of emulating those of the natural origin products. The present invention thus provides a novel solution to the problem of patchouli oil odor reconstitution.

The odor properties of the other compounds (I) according to the invention are presented further on, upon description of their preparation. In addition to the patchouli note which is common to all of them, each of these compounds develops other distinctive olfactive characters, such that the use of all these compounds in perfumery allows a varied choice of odor nuances, and consequently of applications, when composing patchouli type fragrant products.

As a result of their odor qualities, compounds (I) are convenient both for fine perfumery applications and for perfuming functional products. They can therefore be used with advantage in the preparation of perfuming bases and compositions, perfumes and colognes, as well as for perfuming various articles such as soaps, bath or shower gels, shampoos or other haircare products, body or air deodorants and cosmetic preparations. Detergents or fabric softeners, or yet household products can also be conveniently perfumed by way of the compounds of the invention.

In the forementioned applications, compounds (I) may be used alone or, as is more usual in perfumery, in admixture with other perfuming ingredients, solvents or adjuvants currently employed. A more detailed description of the nature of the latter is not warranted here, the man in the art being well up to the task of choosing them as a function of the desired fragrance effect. In order to do this, he may, for example, resort to such reference works as the book by S. Arctander, Perfume and Flavor Chemicals, Montclair, N.J. USA (1976).

The desired olfactive effect also determines the choice of the proportions in which the compounds according to the invention can be used for the abovementioned applications, proportions which are moreover dependent on the nature of the other ingredients present in a given composition.

These proportions can therefore vary in a wide range of values. Nevertheless, by way of example, one can cite concentrations of the order of 5 to 10%, or even 20% by weight, relative to the weight of the composition into which the compounds (I) are incorporated. Typically, much lower concentrations will normally be used when employing these compounds for perfuming the variety of the above-mentioned consumer products.

The compounds of the invention are prepared from the ketones of formula

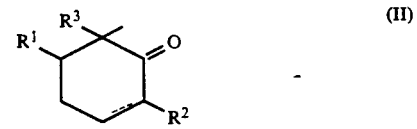

wherein the dotted line and symbols $R^1$ to $R^3$ have the meaning indicated in formula (I), by reacting said ketones with tert-butyl-lithium, in an inert organic solvent. Alternatively, one can use tert-butyl-magnesium under similar conditions, or under the usual conditions of the so-called Barbier reaction [see, for example, J. March, Advanced Organic Chemistry, 3rd ed., page 817, Wiley Interscience, N.J. (1985)]. Starting ketones (II) are either commercially available products, or can be prepared by prior art methods.

The general method for the preparation of compounds (I) is described hereinafter, by reference to the particular case of 1-tert-butyl-2,6,6-trimethyl-2-cyclohexen-1-ol A four-neck flask, equipped with a magnetic stirrer and under argon, was charged with 13.8 g (0.1 mole) of 2,6,6-trimethyl-2-cyclohexen-1-one (see DE-PS-25 47 223) in solution in 100 ml of diethyl ether. 100 Ml (0.14 mole) of tert-butyl-lithium, 1.4N in pentane (Fluka) solution, were added thereto, dropwise and at −40° C. Stirring was maintained for a further 3 h while letting the temperature increase up to 20° C. The reaction mixture was then poured into ice (100 ml), extracted with ether (2×100 ml), and the organic layers were successively washed with 1N HCl (50 ml), NaHCO$_3$ (50 ml) and water saturated with salt (2×50 ml), then dried (MgSO$_4$) and concentrated under reduced pressure.

There were obtained 18.8 g of concentrate, which was distilled on a Vigreux column (10 cm) to yield the 3 following fractions (pressure: 18×10$^2$ Pa):

| Fraction 1 | 80–84° C. | (bath→100° C.) | 0.3 g of starting product |
|---|---|---|---|
| Fraction 2 | 84–110° C. | (100→126° C.) | 0.4 g |
| Fraction 3 | 110–112° C. | (126→134° C.) | 13.5 g of a mixture containing 86% of the desired product and 10% of a by-product and 1.4 g of residue. |

Distilled Fraction 3 was then submitted to chromatography on silica sel, Merck, 0.2–0.063, ∼270 g (20 times), using a 98:2 mixture of cyclohexane/ether as eluting agent, to yield a fraction enriched in the desired product which, after bulb-to-bulb distillation (130°–150° C./18×10$^2$ Pa), provided 7.3 g of 97% pure 1-tert-butyl-2,6,6-trimethyl-2-cyclohexen-1-ol (yield: 37%).

Analytical data:
NMR($^1$H,360 MHz,CDCl$_3$): 0.94(s,3H); 1.09(s,9H); 1.12(s,3H); 1.35(m,1H); 1.80(d,finely divided,J=2 Hz,3H); 2.07(m,2H); 2.14(m,1H) δ ppm
NMR($^{13}$C,90.5 MHz,CDCl$_3$): 137.6(s); 124.5(d); 81.2(s); 42.8(s); 41.1(s); 34.4(t); 29.4(q); 28.6(q); 27.6(q); 22.6(t); 22.1(q) δ ppm
MS: 196(M$^+$,0), 178(1), 163(1), 139(29), 121(14), 107(7), 95(48), 83(19), 67(6), 55(15), 43(100).
Odor: described above.

Following an analogous procedure to that described above, but using the appropriate ketone (II) as starting product, the following compounds were also prepared:

1-tert-butyl-2,2,6-trimethyl-1-cyclohexanol

Prepared from 2,6,6-trimethyl-1-cyclohexanone (Aldrich).
Analytical data:
NMR($^1$H,360 MHz, CDCl$_3$): 0.97(d,J=14 Hz,1H); 1.06(d,J=7 Hz,3H); 1.12(s, 12H); 1.17(s,3H); 1.27–1.53(m,4H); 1.75(dxdxd,J$_1$=14,J$_2$=14,J$_3$=3 Hz,1H); 2.02(m,1H) δ ppm
NMR($^{13}$C, 90.5 MHz, CDCl$_3$): 80.8(s); 43.6(t); 42.0(s); 41.4(s); 35.7(d); 33.4(t); 30.6(3xq); 29.0(q); 24.5(q); 21.9(t); 21.4(q) ppm
MS: 198(M$^+$,1), 180(1), 165(1), 141(33), 123(64), 113(29), 99(15), 83(46), 71(71), 57(100), 43(86).
Odor: woody, patchouli, celluloïd, geonol.

1-tert-butyl-2-ethyl-6,6-dimethyl-2-cyclohexen-1-ol

Prepared from 2-ethyl-6,6-dimethyl-2-cyclohexen-1-one (see H. Kopf and N. Krause, Liebigs Ann. Chem. 1987, 943).
Analytical data:
NMR($^1$H,360 MHz,CDCl$_3$): 0.95(s,3H); 1.03(t,J=7 Hz,3H); 1.06(s,9H); 1.12(s,3H); 1.36(m,1H); 1.99–2.24(m,5H); 5.48(broad s,1H) δ ppm
MS: 210(M$^+$,0), 192(1), 177(1), 153(46), 135(9), 121(4), 109(50), 97(21), 81(7), 69(15), 57(33), 43(100).
Odor: woody, slightly amber, cedar, patchouli, pungent-irritant, acidic.

1-tert-butyl-2,5,6-trimethyl-2-cyclohexen-1-ol

Prepared from 2,5,6-trimethyl-2-cyclohexen-1-one (see, for example, US Publ. Pat. Appl. B 501,128). The product obtained was a mixture of 3 stereoisomers (∼20%–60%–20%).
Analytical data:
NMR($^1$H,360 MHz,CDCl$_3$): mixture of 3 isomers: 0.79(d,J=7 Hz); 0.90(d,J=7 Hz); 0.97(s); 1.02(d,J=7 Hz); 1.04(s); 1.05(s); 1.05–1.25(m); 1.39–1.54(m); 1.67–2.63(m); 1.79(broad s); 1.83(broad s); 5.42(broad s); 5.47(broad s); 5.83(d,J=8 Hz) δ ppm Isomer 1

MS: 196(M$^+$,0), 178(5), 163(5), 149(1), 139(97), 121(41), 105(26), 95(53), 79(16), 69(19), 57(60), 43(100)

Isomer 2

MS: 196(M$^+$,1), 178(10), 163(10), 149(2), 139(100), 121(52), 107(25), 95(47), 83(23), 69(31), 57(64), 43(73)

Isomer 3

MS: 196(M$^+$,1), 178(16), 163(9), 149(1), 139(87), 121(51), 107(29), 95(43), 83(25), 69(54), 57(100), 43(73).
Odor: woody, slightly amber, cedar, patchouli, acidic, pungent-irritant.

cis-1-tert-butyl-2,5,6-tetramethyl-2-cyclohexen-1-ol

Prepared from 2,5,6,6-tetramethyl-2-cyclohexen-1-one (see, for example, DE-OS 24 44 585).
Analytical data:
NMR($^1$H,360 MHz,CDCl$_3$): 0.78(s,3H); 0.86(d,J=7 Hz,3H); 1.09(s,9H); 1.50–1.63(m,1H); 1.79(broad s,3H); 2.09–2.21(m,1H); 2.33–2.49(m,1H); 5.47(broad s,1H) δ ppm
NMR($^{13}$C,90.5 MHz,CDCl$_3$): 137.5(s); 124.9(d); 82.0(s); 44.6(s); 43.0(s); 33.3(d+t); 30.2(3xq); 24.8(q); 22.3(q); 19.8(q); 16.9(q) δ ppm
MS: 210(M$^+$,0), 192(2), 177(3), 163(1), 153(51), 135(25), 121(17), 109(48), 91(17), 82(61), 69(11), 57(23), 43(100).
Odor: woody, patchouli, mouldy.

1-tert-butyl-2,2,3,6-tetramethyl-1-cyclohexanol

Prepared from 2,5,6,6-tetramethyl-1-cyclohexanone (see DE-OS 24 44 585).
Analytical data:
NMR($^1$H,360 MHz,CDCl$_3$): 0.81(d,J=7 Hz,3H); 1.02(s,3H); 1.06(d,J=7 Hz,3H); 1.10(s,3H); 1.14(s,9H); 1.38–1.49(m,3H); 1.62–1.77(m,1H); 2.02–2.15(m,1H) δ ppm
NMR($^{13}$C,90.5 MHz,CDCl$_3$): 81.1(s); 44.5(s); 42.6(s); 38.0(d); 35.7(d); 31.4(t); 30.3(3xq); 29.7(t); 24.4(q); 21.4(q); 17.9(q); 17.1(q) δ ppm
MS: 212(M$^+$,1), 194(1), 179(1), 155(26), 137(75), 127(20), 109(11), 96(32), 85(51), 71(63), 57(95), 43(100).
Odor: amber, mouldy, woody, earthy.

The invention will now be described in further detail by way of the following examples.

EXAMPLE 1

Perfuming Composition for Shampoo

A base perfuming composition intended for a shampoo was prepared by admixing the following ingredients:

| Ingredients | Parts by weight |
| --- | --- |
| Phenyl ethyl alcohol | 130 |
| Ethylene brassylate | 20 |
| Aspic essential oil | 80 |
| Synth. geraniol | 80 |
| Synth. bergamote oil | 80 |
| Linalyl acetate | 60 |
| Synth. geranium oil | 60 |
| 10%* Oakmoss absolute | 60 |
| Patchouli essential oil | 40 |
| 10%* Labdanum resinoïd | 40 |
| p-tert-Butylcyclohexyl acetate | 30 |
| Galaxolide ® 50[1)] | 50 |
| Coumarine | 30 |
| Linalol | 60 |
| Terpineol | 30 |
| Methylisoeugenol | 30 |
| Rosemary essential oil | 20 |
| 10%* Galbanum essential oil | 20 |
| Sandela ®[2)] | 20 |
| 10%* Synth. civet | 20 |
| Synth. neroli oil | 15 |
| Lavandin absolute | 10 |
| Lilial ®[3)] | 10 |
| Myrtle essential oil | 5 |
| Total | 1000 |

*in dipropylene glycol (DIPG)
[1)]1,3,4,6,7,8-hexahydro-4,6,6,7,8,8-hexamethyl-cyclopenta[g]isochromene; origin: IFF Inc., USA
[2)]3-(isocamphyl-5)-cyclohexan-1-ol; origin: L. Givaudan, Vernier, Switzerland
[3)]p-tert-butyl-α-methylhydrocinnamaldehyde; origin: L. Givaudan, Vernier, Switzerland Upon replacement, in this woody, herbaceous, floral type base composition, of the 4% by weight of patchouli essential oil by the same amount of 1-tert-butyl-2,6,6-trimethyl-2-cyclohexen-1-ol, a new composition was obtained which possessed a clear patchouli odor character, but less earthy and woodier than the olfactive character imparted by the natural origin oil.

EXAMPLE 2

Perfuming Composition of the Feminine Type

A base perfuming composition intended for a feminine-type perfume was prepared by admixing the following ingredients:

| Ingredients | Parts by weight |
| --- | --- |
| Coriander essential oil | 100 |
| Benzyl acetate | 100 |
| Styrallyl acetate | 80 |
| Vetyveryl acetate | 1150 |
| 10%* Undecylenic aldehyde | 150 |
| Hexylcinnamic aldehyde | 100 |
| Citronellol | 250 |
| Dioxycarbinol | 450 |
| Exaltolide ®[1)] | 200 |
| Geraniol | 300 |
| Iralia ®[2)] | 50 |
| Jasmic absolute | 150 |
| 10%* Labdanum ciste | 200 |
| Linalol | 200 |
| Lyral ®[3)] | 700 |
| 50%* Dalma oakmoss absolute | 200 |
| Hedione ®[4)] | 3000 |
| Methyl octylcarbonate | 200 |
| 10%* Rose oxide | 25 |
| Phenylethyl alcohol | 450 |
| Rosinol cryst. | 50 |
| Amyl salicylate | 75 |
| Benzyl salicylate | 200 |
| 1%* Vanillin | 220 |
| α-Ionone | 200 |
| Ylang essential oil | 200 |
| Patchouli essential oil | 1000 |
| Total | 10000 |

*in dipropylene glycol (DIPG)
[1)]pentadecanolide; origin: Firmenich SA, Geneva, Switzerland
[2)]methylionone; origin: Firmenich SA, Geneva, Switzerland
[3)]4-(4-hydroxy-4-methylpentyl)-3-cyclohexene-1-carboxaldehyde: origin: IFF Inc., USA
[4)]methyl dihydrojasmonate; origin: Firmenich SA, Geneva, Switzerland Upon replacing, in this woody, aromatic, floral type base composition the 10% by weight of patchouli essential oil by 5% by weight of 1-tert-butyl-2,6,6-trimethyl-2-cyclohexen-1-ol, a new composition was obtained, the patchouli character of which came up reinforced and accompanied by a very natural rooty, woody note. In addition, the new composition had much greater impact than the base composition.

What we claim is:

1. A compound of the formula

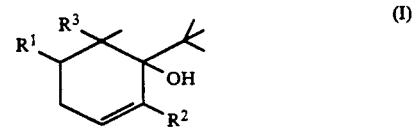

wherein symbols $R^1$ and $R^3$ represent each a hydrogen atom or a methyl radical and symbol $R^2$ represents a lower alkyl radical.

2. 1-tert-Butyl-2,6,6-trimethyl-2-cyclohexen-1-ol.

3. A method to confer, improve, enhance or modify the patchouli-type odor character of a perfuming composition or a perfumed article, which method comprises adding to said composition or article a fragrance effective amount of a compound of formula (I) as defined in claim 1.

4. A method to confer, improve, enhance or modify the patchouli-type odor character of a perfuming composition or a perfumed article, which method comprises adding to said composition or article a fragrance effective amount of 1-tert-butyl-2,6,6-trimethyl-2-cyclohexen-1-ol.

5. A perfuming composition or a perfumed article containing as a perfuming ingredient a compound of formula (I) as defined in claim 1.

6. A perfuming composition or a perfumed article containing as a perfuming ingredient 1-tert-butyl-2,6,6-trimethyl-2-cyclohexen-1-ol.

7. A perfumed article according to claim 5 or 6, in the form of a perfume or cologne, a soap, a bath or shower gel, a shampoo or other hair-care product, a body or air deodorant, a cosmetic preparation, a detergent or a fabric softener, or a household product.

8. A perfuming composition according to claim 5 or 6 which exhibits a patchouli-type odor character.

* * * * *